(12) United States Patent
Dong et al.

(10) Patent No.: US 10,596,098 B2
(45) Date of Patent: Mar. 24, 2020

(54) DURABLE DENTAL FILM-FORMING COMPOSITION AND USES THEREOF

(71) Applicant: COLGATE-PALMOLIVE COMPANY, New York, NY (US)

(72) Inventors: Rong Dong, East Brunswick, NJ (US); Guofeng Xu, Plainsboro, NJ (US); Shaotang Yuan, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/344,394

(22) Filed: Nov. 4, 2016

(65) Prior Publication Data

US 2017/0128346 A1  May 11, 2017

Related U.S. Application Data

(60) Provisional application No. 62/251,294, filed on Nov. 5, 2015.

(51) Int. Cl.
| | | |
|---|---|---|
| *A61Q 11/00* | (2006.01) | |
| *A61K 8/81* | (2006.01) | |
| *A61Q 11/02* | (2006.01) | |
| *A61K 8/29* | (2006.01) | |
| *A61K 8/02* | (2006.01) | |
| *A61K 8/97* | (2017.01) | |

(52) U.S. Cl.
CPC .......... *A61K 8/8164* (2013.01); *A61K 8/0216* (2013.01); *A61K 8/29* (2013.01); *A61K 8/8158* (2013.01); *A61K 8/97* (2013.01); *A61Q 11/00* (2013.01); *A61Q 11/02* (2013.01); *A61K 2800/594* (2013.01)

(58) Field of Classification Search
None
See application file for complete search history.

(56) References Cited

U.S. PATENT DOCUMENTS

| | | |
|---|---|---|
| 3,507,822 A | 4/1970 | Miyami |
| 4,274,879 A | 6/1981 | Irvine |
| 4,330,514 A | 5/1982 | Hirosi et al. |
| 5,122,370 A | 6/1992 | Merianos et al. |
| 5,776,435 A | 7/1998 | Gaffar et al. |
| 8,852,561 B2 | 10/2014 | Wagner et al. |
| 8,883,212 B2 * | 11/2014 | Pillai ..................... A61Q 11/00 424/401 |
| 2005/0038181 A1 | 2/2005 | Chopra et al. |
| 2006/0141423 A1 * | 6/2006 | Brown ................. A61C 19/004 433/215 |
| 2007/0122360 A1 | 5/2007 | Takayuki et al. |
| 2011/0076241 A1 | 3/2011 | Sinichi et al. |
| 2014/0242001 A1 * | 8/2014 | Pillai ..................... A61Q 11/00 424/52 |

FOREIGN PATENT DOCUMENTS

| | | |
|---|---|---|
| EP | 2353576 | 8/2011 |
| WO | WO 2014/127178 | 8/2014 |
| WO | WO 2015/099642 | 7/2015 |

OTHER PUBLICATIONS

International Search Report and Written Opinion in International Application No. PCT/US2016/060692, dated Jan. 30, 2017.

* cited by examiner

*Primary Examiner* — Brian Gulledge

(57) ABSTRACT

Disclosed is a durable dental film-forming composition including an acrylate/octylacrylamide copolymer, wherein the acrylate/octylacrylamide copolymer is present in an amount of about 0.1% to about 50% by weight, an adhesive, and an orally acceptable solvent. Methods of using the composition are also disclosed.

19 Claims, 1 Drawing Sheet

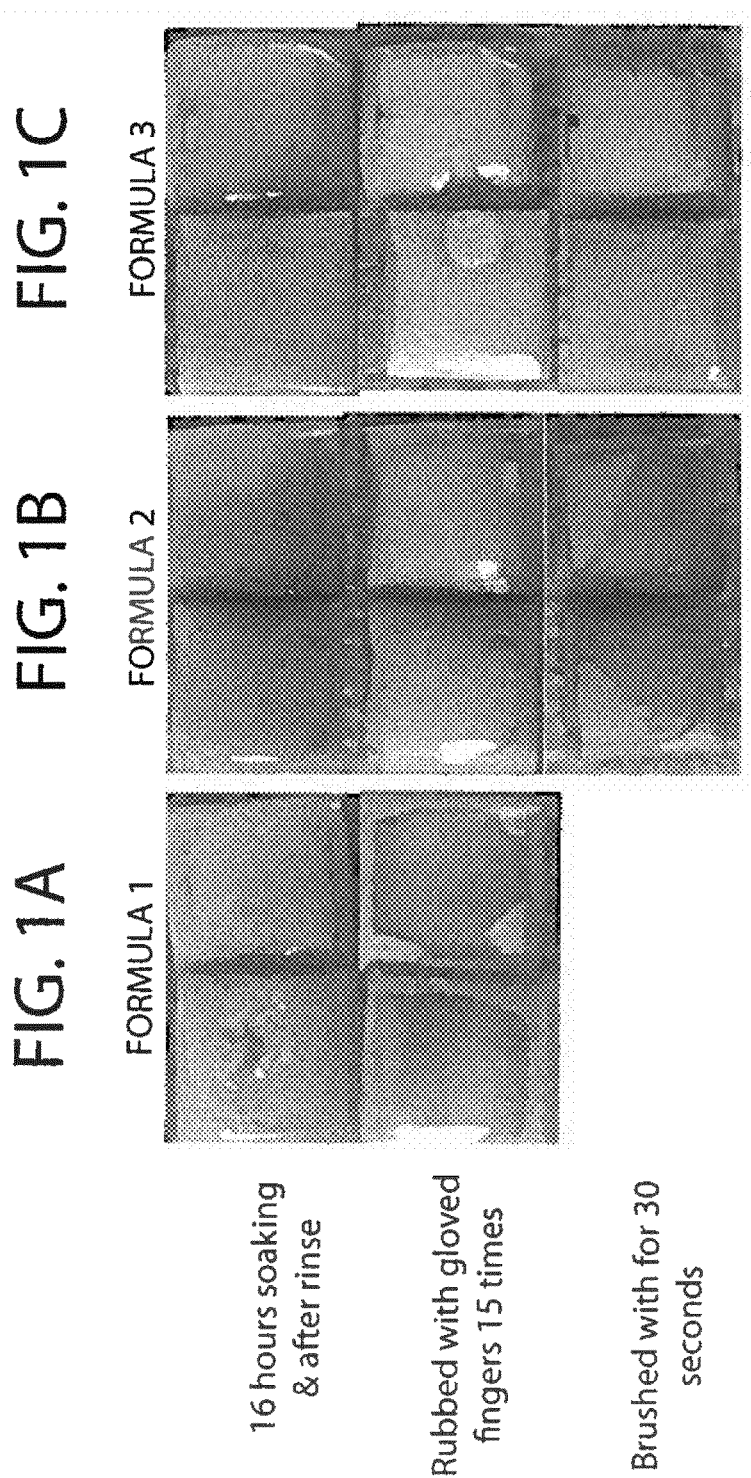

DURABLE DENTAL FILM-FORMING COMPOSITION AND USES THEREOF

CROSS-REFERENCE TO RELATED PATENT APPLICATIONS

This application claims the benefit of priority to U.S. Provisional Patent Application Ser. No. 62/251,294 filed Nov. 5, 2015, the entirety of which is incorporated herein by reference.

BACKGROUND

Polymer delivery systems for application to the teeth have been used to protect the teeth from bacteria and plaque formation, to provide sustained delivery of active agents, such as fluoride or antibacterial agents and to deliver tooth whitening agents to the teeth. However, the prior polymer delivery systems have, in general, not proven sufficiently durable to remain on the teeth for extended periods. The teeth are routinely physically abraded by brushing and chewing and are exposed to a wide range of temperatures and pH levels as a result of eating and drinking. Under ordinary conditions, therefore, most polymers will not remain on the teeth for very long. Accordingly, there is a desire in the art for a robust delivery system that can provide whitening particles and other active ingredients to the teeth, as well as to protect the teeth from plaque and biofilm formation, without rapid delamination during routine activities, such as brushing.

BRIEF SUMMARY

The present disclosure is directed to a durable dental film-forming composition, including: an acrylate/octylacrylamide copolymer, wherein the acrylate/octylacrylamide copolymer is present in an amount of about 0.1% to about 50% by weight, an adhesive and an orally acceptable solvent.

Further areas of applicability of the present disclosure will become apparent from the detailed description provided hereinafter. It should be understood that the detailed description and specific examples, while indicating typical embodiments, are intended for purposes of illustration only and are not intended to limit the scope of the disclosure.

BRIEF DESCRIPTION OF THE DRAWINGS

FIGS. 1A-1C show examples of bovine tooth blocks coated with a prior art dental film-forming composition (FIG. 1A) and two dental film-forming compositions according to the present disclosure (FIGS. 1B-1C) after incubation, rubbing and brushing challenges.

DETAILED DESCRIPTION

The following description of the embodiments is merely exemplary in nature and is in no way intended to limit the disclosure, its application or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Compositions

The present inventors have surprisingly recognized that compositions containing acrylate/octylacrylamide copolymers when combined with adhesives, such as rosin, are more durable than other polymer systems, even after brushing. Accordingly, the present compositions are suitable vehicles for delivery and for the sustained application of whitening and/or therapeutic agents on teeth. The present compositions may also be used to protect teeth from staining and from biofilm and plaque formation, which could otherwise lead to tooth decay and gingivitis.

Polymer/Adhesive Components

The present disclosure is directed to a durable dental film-forming composition, which includes a film-forming polymer. As used herein, a "film forming polymer" is understood to encompass polymers, prepolymers and/or monomers capable of forming alone, or in the presence of at least one additional agent, a continuous and adherent film on a tooth substrate. The term "prepolymer" refers to a system of monomers that have been reacted to an intermediate molecular mass state. This material is capable of further polymerization by reactive groups to reach a fully cured high molecular weight state. As such, mixtures of reactive polymers with unreacted monomers may also be referred to as prepolymers. A "monomer" is a molecule that may bind chemically to other molecules to form a polymer.

Typically, the film-filming polymer used in the present composition is an acrylate/octylacrylamide copolymer. As used herein, an "acrylate/octylacrylamide copolymer" refers to a copolymer of octylacrylamide (for example N-(1,1,3, 3-tetramethylbutyl)-2-propenamide) and one or more monomers selected from acrylic acid, methacrylic acid and their simple esters. In a typical embodiment, the acrylate/octylacrylamide copolymer is 2-Propenoic acid, 2-methyl-, 2-methylpropyl ester, polymer with 2-propenoic acid and N-(1,1,3,3-tetramethylbutyl)-2-propenamide (CAS 129702-02-9), for example, DERMACRYL® 79, which is commercially available from AkzoNobel Company, Surface Chemistry, Amsterdam, Netherlands.

In some embodiments, an acrylate/octylacrylamide copolymer is present in the instant composition in an amount ranging from about 0.1% to about 50% by weight, such as about 5% to about 30% by weight, such as about 5% to about 20% by weight. Typically, the acrylate/octylacrylamide copolymer is present in amounts of less than about 10% by weight, such as about 9% by weight.

The present durable dental film-forming composition also includes an adhesive. The adhesive may be used to improve the adhesion of the film to a substrate, such as a tooth surface and/or to increase the hydrophobicity of the coated film, which in turn contributes to the ability of the film to withstand challenges, such as rubbing or brushing.

Suitable adhesives include alkyd resins, polyvinyl acetaldehydes, polyvinyl alcohols, polyvinyl acetates, poly(ethylene oxide), polyacrylates, ketone resins, polyvinylpyrolidone, polyvinylpyrolidone/vinyl acetate copolymer, polyethylene glycols of 200 to 1000 molecular weight and polyoxyethylene/polyoxypropylene block copolymers (Polyox). Suitable adhesives also include organo phosphoric acid compounds having alkyl groups. The alkyl group includes at least two carbon atoms. Preferred alkyl groups include from 3 to about 30 carbon atoms. Silicone resins are also suitable.

In some embodiments, the adhesive comprises a silicone pressure sensitive adhesive (PSA). PSAs can be produced by condensing a silicone resin and an organosiloxane, such as a polydiorganosiloxane. In some embodiments, the silicone polymers are prepared by mixing a silanol terminated polydiorganosiloxane, such as polydimethyl siloxane, with a silanol-containing silicone resin, whereby the silanol groups of the polydiorganosiloxane undergo a condensation reaction with the silanol groups of the silicone resin so that the polydiorganosiloxane is lightly crosslinked by the silicone resin. A catalyst, for example, an alkaline material, such as ammonia, ammonium hydroxide or ammonium carbonate, can be mixed with the silanol-terminated polydiorganosiloxane and the silicone resin to promote crosslinking. By copolymerizing the silicone resin with the silanol terminated polydiorganosiloxane, a polymer with self-adhering properties and a soft elastomer matrix can be produced.

Suitable PSA polymers in accordance with the present disclosure are described in U.S. Patent Publication No. 2015/0037266 and U.S. Patent Publication No 2005/0038181, which are each incorporated by reference herein in its entirety. Suitable commercially available PSA polymers include BIO-PSA polymers from the Dow Corning Corporation. These PSA polymers are available in three silicone resin to silicone polymer ratios, namely, 65/35 (low tack), 60/40 (medium tack), 55/45 (high tack). Without being bound by theory, it is believed that the variation in the ratio of silicone resin to polydiorganosiloxane results in the different tack properties of the BIO-PSA polymers.

In some embodiments, the adhesive is a synthetic resin. A suitable synthetic resin includes Fluor Protector, which is available from Ivoclar Vivident AG, Liechtenstein.

In some embodiments, the adhesive is a natural resin. Suitable natural resins include, but are not limited to, shellac, rosins and combinations thereof. Shellac is commercially available and may be provided with a solvent (e.g. ethanol). One such commercially available shellac, known as Refined Pharmaceutical Glaze, is available from Mantrose-Haeuser Co., Inc. Westport, Conn.

Suitable rosins, which may be included in the present composition include without limitation, wood rosin, gum rosin, tall oil rosin and mixtures thereof. The suitable rosins may be in a crude or a refined state.

In some embodiments, the rosins, which may be used according to the present disclosure, are at least partially hydrogenated. The more hydrogenated a rosin, the more colorless it will appear to the human eye because the double bonds found in rosins tend to absorb color. Accordingly, when whitening pigments are included in the present compositions as described herein, fully hydrogenated rosins are typically used.

In some embodiments, the rosins are from the class of rosins known in the art as the colophonium class. Members of the colophonium class are non-synthetic naturally-derived sticky resins (e.g., typically derived from various species of pine). Colophonium typically includes a substantial fraction of resin acid components that are isomeric with abietic acid ($C_{20}H_{30}O_2$). Examples of colophonium also may include dihydrobietic acid ($C_{20}H_{32}O_2$) and/or dehydroabietic acid ($C_{20}H_{28}O_2$). Colophonium may range from black to substantially colorless, although resins from this class are typically pale yellow to amber in color and have a density of about 1.07 to about 1.09 g/cm$^3$. Various materials that are individually referred to as "colophonium" include Canadian balsam, Olibanum balsam, Elemi resin, Opopanax resin, Tolu balsam, Peruvian balsam, and POLY-PALE™ resin, which is a partially dimerized rosin available from Eastman Chemical Company, Kingsport, Tenn.

Suitable commercially available rosins include FORAL™ AX-E, a fully hydrogenated tree rosin that has been distilled and dimerized (Eastman Chemical Company). FORAL™ AX-E is nearly colorless and in some embodiments is more stable than colophonium components. FORAL™ AX-E resists oxidation and retains its substantially colorless characteristics over time. Other suitable commercially available rosins include STAYBELITE™ Resin-E, a partially hydrogenated rosin available from Eastman Chemical Company, which also exhibits good oxidation resistance and pale color, although FORAL™ AX-Eis more typically used due to its greater resistance to oxidation and better color retention properties. Additional suitable commercially available rosins include PAMITE™ (tall oil rosin), DYMEREX™ (dimerized rosin), POLYSTIX® 90 (partially dimerized rosin), DRESINATE™ (rosin soap) and PERMALYN™ NC-11 (noncrystalline rosin) all of which are available from Eastman Chemical Company.

The adhesive, such as a rosin, may be present in the instant composition in an amount ranging from about 0.1% to about 25% by weight, such as about 3.0% to about 15%. Typically, the amount of an adhesive in the present compositions is about 4.5% to about 9%.

Orally Acceptable Vehicle

In some embodiments, the film-forming polymer and the adhesive are dispersed or dissolved in an orally acceptable vehicle, which includes a solvent. As used herein, "orally acceptable" means that the composition and the components thereof are safe for use in the mouth at the levels required. The solvent may be ethanol, methanol, isopropanol, butanol, water, acetone, methyl ethyl ketone, ethyl acetate, butyl acetate, cyclohexanone, cyclohexane, methylene chloride, chloroform, carbon tetrachloride, trichloroethylene, perchloroethylene, methyl glycol acetate, toluene, benzene, diethyl ether, benzyl alcohol or combinations thereof. Typically, the orally acceptable solvent is a volatile solvent such as ethanol. In some embodiments, non-volatile, water soluble solvents may be included in the composition of the present disclosure, such as triacetin or glycerin.

The orally acceptable solvent may be present in an amount of about 0.1% to about 99.5% by weight based upon the total weight of the mixture, although about 60% to about 95% is typical, with an amount of 80%-90% by weight being further typical, such as about 85%, such as about 81%, such as about 82%.

In a typical embodiment, the instant durable dental film-forming composition includes an orally acceptable solvent, which is ethanol, in an amount of about 80% to about 82% by weight, about 9.0% by weight of a rosin and about 10% or less by weight of 2-propenoic acid, 2 methyl-, 2-methylpropyl ester, polymer with 2-propenoic acid and N-(1,1,3,3-tetramethylbutyl)-2-propenamide.

In other embodiments, the instant composition further includes a plasticizer for the purpose of modifying a property of the film or for use as e.g., a further solvent, a dispersant, or as another film-forming polymer. These additives are well known in the plastic and film forming arts and include polyethylene glycol (PEG) polypropylene glycol (PPG), PEG/PPG, phthalic esters, phosphoric esters, esters of adipic, azelaic, glutavic or sebacic acid, fatty acid esters citric esters, esters of acetic, propionic or butyric acid, esters of ethylbutyric or ethyl hexanoic acid, glycol esters, benzoic esters, trimellitic esters, sulfonic esters, sulfonamides, anilides, alcohols, ethers and ketones. The plasticizer may be present in an amount of about 0.01% to about 5% by weight based upon the weight of the total mixture, although an amount of 1.0% by weight is typical.

More typically, an alkyl cellulose ether is included in the instant composition. As used herein, an "alkyl cellulose ether" refers to a lower alkyl ether of cellulose, for example, an ethyl cellulose, such as an ethyl cellulose having a degree of ethoxylation of 45%-50% and a viscosity of about 3 to about 70 millipascals-second (5% solution at 25° C. measured in a Ubbelohde viscometer). Suitable alkyl cellulose ethers are commercially available from The Dow Chemical Company, e.g. ETHOCEL™ E7, ETHOCEL™ E22 or ETHOCEL™ E50.

In some examples, the alkyl cellulose ether is present in the instant composition in an amount ranging from about 0.1% to about 20% by weight, such about 1% to about 10% by weight, such as about 2-5% by weight. In some examples, the alkyl cellulose ether is ethyl cellulose.

In some examples, the alkyl group is optionally substituted with a hydroxyl group, e.g., hydroxypropyl cellulose may be used in the present composition. In some embodiments, hydroxypropyl cellulose is present in the instant composition in an amount ranging from about 0.01% to about 1%, such as about 0.25% or such as about 0.5% by weight.

In other embodiments, the present composition includes a combination of ethyl cellulose and a hydroxyalkyl cellulose ether, e.g., hydroxypropyl cellulose. The ethyl cellulose and hydroxypropyl cellulose may be present in the instant composition in a ratio of about 2:1 to about 30:1, such as about 10:1, such as about 7.5:1. In some embodiments, the present composition includes about 1.5% ethyl cellulose and about 0.2% hydroxypropyl cellulose.

In some embodiments, the orally acceptable vehicle may further comprise surfactants. In some embodiments, surfactants enhance stability of the formulation and help clean the oral cavity surfaces through detergency. Surface active agents generally achieve increased prophylactic action by thoroughly dispersing the whitening agent throughout the oral cavity. In some embodiments, suitable surface active agents may function as a surface active agent, emulsifier, and/or foam modulator.

Any orally acceptable surfactant, most of which are anionic, nonionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium cocoyl monoglyceride sulfonate, sodium lauryl sarcosinate, sodium lauryl isoethionate, sodium laureth carboxylate and sodium dodecyl benzenesulfonate. Suitable nonionic surfactants include without limitation poloxamers, polyoxyethylene sorbitan esters, such as TWEEN™ 80, fatty alcohol ethoxylates, alkylphenol ethoxylates, tertiary amine oxides, tertiary phosphine oxides, dialkyl sulfoxides and the like. Suitable amphoteric surfactants include, without limitation, derivatives of $C_{8-20}$ aliphatic secondary and tertiary amines having an anionic group such as carboxylate, sulfate, sulfonate, phosphate or phosphonate. A suitable example is cocoamidopropyl betaine.

In some embodiments, one or more surfactants may be present in a total amount of from about 0.1% to about 4% by weight. In some embodiments, one or more surfactants may be present in a total amount from about 0.2% to about 2% by weight, such as about 0.5% by weight.

Flavoring agents may also be included in the orally acceptable vehicle. Useful flavoring agents include any material or mixture of materials operable to enhance the taste of the composition. Any orally acceptable natural or synthetic flavoring agent can be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and mixtures thereof. Also encompassed within flavoring agents herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, x-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA) and mixtures thereof.

In some embodiments, one or more flavoring agents are optionally present in a total amount of about 0.01% to about 5% w/w. In some embodiments, one or more flavoring agents are optionally present in a total amount of about 0.05% to about 2% w/w. In some embodiments, one or more flavoring agents are optionally present in a total amount of about 0.1% to about 2.5% w/w. In some embodiments, one or more flavoring agents are optionally present in a total amount from about 0.1% to about 0.5% w/w. In some embodiments, one or more flavoring agents are optionally present in the total amount of about 1.4% w/w.

Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones and mixtures thereof. Some embodiments optionally comprise one or more sweeteners. In some embodiments, the one or more optional sweeteners are present in a total amount from about 0.005% to about 5% w/w. In some embodiments, the one or more optional sweeteners are present in a total amount from about 0.01 to about 1% w/w.

Colorants, mouth-feel agents and/or others additives may also be included, if desired, in the present compositions.

The present durable dental film-forming composition may be in a liquid or gel form. In some embodiments, the viscosity of the present durable dental film-forming composition ranges from about 1.1 mPa·S to about 1000 mPa·S, more typically about 1.1 mPa·S to about 100 mPa·S and even more typically about 3 mPa·S to about 15 mPa·S.

Whitening Agents

As used herein a "whitening agent" is a material that affects the whitening of a tooth surface to which it is applied. Any whitening agent known or developed in the art may be used in the present compositions.

For example, in some embodiments, the present compositions include a whitening pigment. In some embodiments, the whitening pigments include particles ranging in size from about 0.1 µm to about 10 µm with a refractive index greater than about 1.2. Suitable whitening agents include, without limitation, titanium dioxide particles, zinc oxide particles, aluminum oxide particles, tin oxide particles, calcium oxide particles, magnesium oxide particles, barium oxide particles, silica particles, zirconium silicate particles, mica particles, talc particles, tetracalcium phosphate particles, amorphous calcium phosphate particles, alpha-tricalcium phosphate particles, beta-tricalcium phosphate particles, hydroxylapatite particles, calcium carbonate particles, zinc phosphate particles, silicon dioxide particles, zirconium silicate particles and combinations thereof. The whitening pigment, such as titanium dioxide particles, may be in an amount that is sufficient to whiten the teeth.

In some embodiments, the whitening agent is hydroxylapatite. The hydroxylapatite whitening agent used with the composition of the present disclosure may be a calcium phosphate salt having the chemical formula $Ca_5(OH)(PO_4)_3$. The preparation of hydroxylapatite is well known in the art and is disclosed, for example, in U.S. Pat. Nos. 4,274,879 and 4,330,514, which is herein incorporated by reference in its entirety. If present, the hydroxylapatite whitening agent may be at a concentration ranging from about 0.5% to about 60% by weight, typically about 15% to about 40% by weight.

In other embodiments, the whitening agent is a pigment that imparts a non-white color to the teeth to further enhance the whiteness of the teeth. As is known in the art, the visual perception of a white substance can be altered through the deposition of an optical brightener, a blue pigment or a blue dye. This effect is commonly used in laundry detergent products to make white clothes appear "whiter" to the human eye. The same concept has been applied to tooth whitening. See PCT Publication No. WO 2015/099642 to Colgate-Palmolive Company, which is herein incorporated by reference in its entirety.

Typically, the pigment imparting color is violet or blue, such as Pigment Blue 15, more typically Pigment Blue 15:1, 15:2, 15:3, 15:4, 15:5 or 15:6, most typically 15:1.

The amount of pigment which imparts color to the instant composition is about 0.01% to about 0.3%, typically from about 0.01% to about 0.1%, and more typically from about 0.01% to 0.08% by weight, such as about 0.075%.

In some embodiments, the whitening agent is an oxidizing agent, a reducing agent or combinations thereof. In its broadest sense, "oxidizing agent" is intended to include those compounds which can accept an electron from another molecule in the environment of the oral cavity without having a deleterious or unacceptably harmful effect on the oral cavity in normal and accepted use.

Oxidizing agents suitable for use with the present composition includes peroxides, chlorites and hypochlorites. Examples of suitable chlorites and hypochlorites include those having alkali or alkaline metal cations and include calcium chlorite, barium chlorite, magnesium chlorite, lithium chlorite, sodium chlorite, potassium chlorite, calcium hypochlorite, barium hypochlorite, magnesium hypochlorite, lithium hypochlorite, lithium hypochlorite, and sodium hypochlorite.

In various embodiments, the whitening agent comprises a peroxide compound. As referred to herein, a "peroxide compound" is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, monoperoxyphthalate and mixtures thereof. Peroxy acids and their salts include organic peroxy acids, such as alkyl peroxy acids and monoperoxyphthalate and mixtures thereof, as well as inorganic peroxy acid salts, such as persulfate, dipersulfate, percarbonate, perphosphate, perborate and persilicate salts of alkali and alkaline earth metals such as lithium, potassium, sodium, magnesium, calcium and barium, and mixtures thereof. Typically, the peroxide compound comprises hydrogen peroxide, urea peroxide, sodium percarbonate or mixtures thereof.

In other embodiments, the whitening agent is a reducing agent. In its broadest sense, this term is intended to include those compounds which can donate an electron to another molecule in the environment of the oral cavity without having a deleterious or unacceptably harmful affect on the oral cavity in normal and accepted use. Synonyms for this term are preservatives or anti-oxidizing agents. There are numerous compounds which have been proven to be useful as reducing agents. A list of such compounds currently recognized for this purpose can be found in reference manuals and compendia covering pharmaceutical and oral care products. Suitable examples include vitamin C and its esters, vitamin E, the benzoates and hydroxybenzoates, butylated hydroxytoluene (BHT), butylated hydroxyanisole (BHA) and other reducing phenols, derivatives of dihydroxyquinoline, derivatives of polymerized 2,2,4-trimethyl-1,2-dihydroquinoline and alkyl gallate such as dodecyl gallate, ethyl gallate, octyl gallate and propyl gallate. In some embodiments, vitamin C, vitamin E, BHA, BHT, propyl gallate and combinations thereof are used.

In various embodiments, the oxidizing or reducing whitening agent comprises from about 4.1% to about 50% w/w, such as about 4.1% to about 40% w/w, such as about 4.1% to about 30% w/w of the present durable dental film-forming compositions. In other embodiments, the whitening agent, such as a peroxide, is present in a low concentration, e.g. about 0.01% to about 4%, such as about 0.1% to about 4%, such as about 0.01% to about 3%, such as about 0.05% to about 3%, such as about 0.075% to about 2%, such as about 0.1% to about 1.5%, such as about 0.01% to about 0.3%, such as about 0.1% to about 0.3% or about 0.1%.

Complexed Whitening Agents

In some embodiments, the present compositions include a whitening complex. As used herein a "whitening complex" includes a whitening agent as described herein complexed with a polymer or copolymer, which releases the whitening agent upon exposure to highly aqueous environments, such as in the oral cavity. As used herein, a "complex" is an entity formed by a loose association involving two or more molecular entities (ionic or uncharged), e.g., a whitening agent and a polymer.

The whitening agent associated with a polymer of the present application includes polymers that are typically cross-linked and are capable of absorbing, adsorbing, complexing or otherwise associating with the provided whitening agent of the present application. Further, the polymer is suitably facilitated to retain the whitening agent of the present application. Such retained whitening agent source discharges the whitening agent when it is applied onto the teeth for whitening.

Suitable polymers and co-polymers include N-vinyl lactam based polymers and copolymers. Typically, the polymer is a cross-linked polyvinylpyrrolidone, also known as poly-N-vinyl-poly-2-pyrrolidone, and commonly abbreviated to cross-linked "PVP." PVP generally refers to a polymer containing vinylpyrrolidone (also referred to as N-vinylpyrrolidone, N-vinyl-2-pyrrolidone and N-vinyl-2-pyrrolidinone) as a monomeric unit. The monomeric unit consists of a polar imide group, four non-polar methylene groups and a non-polar methane group. Cross linked PVP includes those commercially available as Kollidon® and Luvicross®, marketed by BASF, Mount Olive, N.J., USA and PolyPlasdone® INF-10, marketed by ISP Corporation, Wayne, N.J., USA.

In some embodiments, the cross-linked polyvinylpyrrolidone is complexed with a peroxide whitening agent, such as hydrogen peroxide (hereinafter "PVP-$H_2O_2$"). Upon exposure to highly aqueous environments, such as in the oral cavity, the PVP-$H_2O_2$ dissociates into individual species (PVP polymer and $H_2O_2$). Suitable cross-linked complexes of PVP-$H_2O_2$ are known in the art and are disclosed, for example, in U.S. Pat. No. 5,122,370, which is herein incorporated by reference in its entirety. Commercially available complexes of hydrogen peroxide adsorbed to cross-linked polyvinylpyrrolidone include, for example, Peroxydone XL-10 and Peroxydone K-30, marketed by ISP Corporation, Wayne, N.J., USA.

Some embodiments of the present disclosure provide a composition comprising from about 0.05% to about 25% by weight cross-linked polyvinylpyrrolidone complexed with a whitening agent. Other embodiments provide a durable dental film-forming composition comprising from about 0.1% to about 15% by weight cross-linked polyvinylpyrrolidone complexed with a whitening agent. Still other embodiments provide a durable dental film-forming composition comprising from about 0.25% to about 10% by weight cross-linked polyvinylpyrrolidone complexed with a whitening agent.

Therapeutic Agents

In some embodiments, the durable dental film-forming composition includes a therapeutic agent. Suitable therapeutic agents include a source of fluoride ions. In some embodiments, the source of fluoride ions is selected from fluoride, monofluorophosphate (MFP) and fluorosilicate salts. In some embodiments, one or more fluoride ion-releasing compounds are optionally present in an amount providing a total of 100 to 20,000 ppm, 200 to 5,000 ppm, or 500 to 2,500 ppm fluoride ions. If present, the amount of fluoride in the present composition ranges from about 0.1% to 1.1%, typically about 1.1% by weight.

The therapeutic agent also may include a stannous ion or a stannous ion source to mitigate calcium loss. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%.

The therapeutic agent may also include an antimicrobial (e.g., antibacterial) agent, such as triclosan. An illustrative list of useful antibacterial agents is provided in U.S. Pat. No. 5,776,435 to Gaffar et al., the contents of which are incorporated herein by reference. One or more antimicrobial agents may be present in an antimicrobial effective total amount of typically about 0.05% to about 10%, for example about 0.1% to about 3%.

Other therapeutic agents include without limitation calcium ion sources, e.g. calcium carbonate, a zinc ion source, e.g., zinc citrate, a potassium ion source, e.g., potassium chloride or combinations thereof. If present, the amount of ion source in the present composition ranges from about 0.1% to 5%, typically about 1% by weight. A basic amino acid, e.g., arginine in free or salt form, may also be used as a therapeutic agent.

Methods

In various embodiments, the present disclosure provides methods of protecting a tooth surface from stains or bacteria and/or methods of whitening a tooth surface in a human or animal subject by applying a durable dental film-forming composition of the present disclosure onto a tooth surface. As used herein "animal subject" includes non-human mammals such as canines, felines and horses. The durable dental film-forming composition is contacted with an oral surface of the mammalian subject to thereby whiten teeth in a highly efficacious manner.

In some embodiments, the durable dental film-forming composition, such as a liquid or gel, may be applied directly to the teeth using a delivery device, such as a pen, e.g., a COLGATE® whitening pen or a COLGATE® ACTIS™ whitening pen, Colgate-Palmolive Company, New York, N.Y., a liquid stick having an applicator, such as a felt tip, felt pads, brush, roller ball, or non-woven pad, sufficient to effect whitening. Spray coating may also be used.

Another convenient way of applying the instant composition is to provide a tube having a wicking device to deliver the present composition to a tip which protrudes from the tube. The tip is then pressed against the tooth to deliver the instant durable dental film-forming composition. This type of device is similar to a "magic marker."

Some embodiments provide a method wherein a delivery device, such as a whitening pen is stored within an oral care implement, such as a toothbrush. In some embodiments, the delivery device, such as a whitening pen is removed from the oral care implement prior to application of the composition to the tooth. In some embodiments, the composition is applied to the tooth after brushing with the oral care implement.

The examples and other embodiments described herein are exemplary and not intended to be limiting in describing the full scope of compositions and methods of this disclosure. Equivalent changes, modifications and variations of specific embodiments, materials, compositions and methods may be made within the scope of the present disclosure, with substantially similar results.

EXAMPLES

Example 1. Formulations

Dental film-forming compositions were prepared using the following ingredients in the amounts specified in Tables 1-3: Anhydrous Ethyl Alcohol, 200 Proof, PHARMCO-AAPER Company, Brookfield, Conn.; Acrylates/Octylacrylamide Copolymer, DERMACRYL® 79, AkzoNobel Company, Surface Chemistry, Amsterdam, Netherlands; Hydrogenated Rosin, FORAL™ AX-E Fully Hydrogenated Rosin, Eastman Chemical Company, Kingsport, Tenn. and titanium dioxide (TiO$_2$), KRONOS Worldwide Inc., Chelmsford, Mass.

The ingredients specified in each of Tables 1-3 were combined in a spin mix jar and mixed at 3540 revolutions per minute (rpm) for four minutes. As is indicated in Table 1, below, Formula 1 contains only the film-forming polymer, DERMACRYL® 79, titanium dioxide (TiO$_2$) and solvent (Ethanol, EtOH). As indicated in Tables 2 and 3, below, Formula 2 and Formula 3 each contains the same ingredients as those of Formula 1, except that Formulas 2 and 3 further contain fully hydrogenated rosin.

TABLE 1

| Formula 1 | % | Weight (g) |
|---|---|---|
| DERMACRYL ®79 | 10.0% | 1.0 |
| TiO$_2$ | 1.0% | 0.1 |
| Ethanol | 89.0% | 8.9 |
| Total | 100.00% | 10 |

TABLE 2

| Formula 2 | % | Weight (g) |
|---|---|---|
| DERMACRYL ®79 | 9.0% | 0.9 |
| Hydrogenated Rosin | 9.0% | 0.9 |
| TiO$_2$ | 1.0% | 0.1 |
| Ethanol | 81.0% | 8.1 |
| Total | 100.00% | 10 |

TABLE 3

| Formula 3 | % | Weight (g) |
|---|---|---|
| DERMACRYL ®79 | 9.0% | 0.9 |
| Hydrogenated Rosin | 4.5% | 0.45 |
| TiO$_2$ | 1.0% | 0.1 |
| Ethanol | 85.5% | 8.55 |
| Total | 100.00% | 10 |

Example 2. Durability Testing of the Formulations

Each of the Formulas was gently shaken before spray coating the Formulas onto stained bovine tooth blocks (six teeth per block) using an airbrush with a 0.2 mm nozzle at maximum pressure (Master Airbrush® Brand Model VC16-B22 Airbrushing System and a MAS KIT-VC16 Black Portable Mini Airbrush Air Compressor). For each formula, each block of cow teeth was spray coated until the stains were no longer visible.

After spray coating, each bovine tooth block was incubated in 2 milliliters of artificial saliva in a 12-well plate at 37° C. at 48-50 rpm overnight. After 16 hours, the coated teeth were removed from the saliva, rinsed, photographed and then further challenged by rubbing the teeth with gloved fingers, followed by brushing the teeth with a toothbrush and toothpaste.

As shown in FIG. 1A, the bovine teeth spray coated with Formula 1 (which contains the film-forming polymer, DERMACRYL® 79, without the rosin adhesive) exhibit obvious defects and delamination after the overnight incubation, i.e., more than 50% of the coated area. In contrast, the bovine teeth spray coated with Formulas 2 or 3, which each contain DERMACRYL® 79 and Rosin, remain intact. FIG. 1B and FIG. 1C. Further, water droplets were observed on the Formula 2 and Formula 3 coatings, indicating that the surface coatings are hydrophobic. FIG. 1B and FIG. 1C. As noted above, after the incubation and rinsing challenge described above, the bovine tooth blocks were rubbed with gloved fingers fifteen times. As is evident in FIG. 1A, more than 90% of the coating formed using Formula 1 can be easily rubbed off, whereas more than 95% of the coating formed using Formulas 2 and 3 remain intact after rubbing. FIG. 1B and FIG. 1C.

FIG. 1B shows that more than 90% of the coating formed using Formula 2, which includes 9.0% rosin, remains mostly intact even after brushing the teeth for thirty seconds with toothpaste. In contrast, the Formula 3 coating, FIG. 1C, which contains only half as much rosin as Formula 2, i.e., 4.5% is easily removed by brushing. Specifically, FIG. 1C shows that more than 50% of the Formula 3 coating was removed by brushing. The remaining coating may be removed by wiping the tooth surfaces with ethanol or other alcohol.

These Examples demonstrate that coatings formed on teeth using compositions containing a combination of DERMACRYL® 79 and rosin are more durable than those containing only DERMACRYL® 79. As is indicated by the challenge tests, the addition of rosin improves both the adhesion and the water resistance of the coating, which contributes to its improved durability. Accordingly, a consumer may use the present compositions as a film coating on the teeth, without concern that the coating will readily chip or peel during normal daily routines such as eating, drinking and brushing.

What is claimed is:

1. A durable dental film-forming composition, comprising a film-forming polymer, wherein the film-forming polymer comprises an acrylate/octylacrylamide copolymer, wherein the acrylate/octylacrylamide copolymer is present in an amount of 9 or 10% by weight,
an adhesive, wherein the adhesive is a rosin;
a whitening agent; and
an orally acceptable solvent; and wherein the composition does not contain an alkyl cellulose ether.

2. The durable dental film-forming composition of claim 1, wherein the acrylate/octylacrylamide copolymer is 2-propenoic acid, 2 methyl-, 2-methylpropyl ester, polymer with 2-propenoic acid and N-(1,1,3,3-tetramethylbutyl)-2-propenamide.

3. The durable dental film-forming composition of claim 1, wherein the adhesive further comprises at least one selected from the group consisting of a polyvinyl acetaldehyde, a polyvinyl alcohol, a polyvinyl acetate, a poly(ethylene oxide), a polyacrylate, a polyvinylpyrolidone, a polyvinylpyrolidone/vinyl acetate copolymer, a polyoxyethylene/polyoxypropylene block copolymer, a silicone resin and a organo phosphoric acid having alkyl group.

4. The durable dental film-forming composition of claim 1, wherein the adhesive further comprises shellac.

5. The durable dental film-forming of claim 1, wherein the rosin is selected from the group consisting of a gum rosin, a tall oil rosin, a partially dimerized rosin, a wood rosin and mixtures thereof.

6. The durable dental film-forming composition of claim 1, wherein the rosin is a colophonium rosin.

7. The durable dental film-forming composition of claim 1, wherein the rosin is selected from the group consisting of a fully hydrogenated rosin and a partially hydrogenated rosin.

8. The durable dental film-forming composition of claim 1, wherein the rosin is a fully hydrogenated rosin.

9. The durable dental film-forming composition of claim 1, wherein the orally acceptable solvent is ethanol.

10. The durable dental film-forming composition of claim 1,
wherein the rosin is present in the composition in 4.5% to about 9% by weight; and
wherein the orally acceptable solvent is present in the composition in an amount ranging from about 80% to about 82% and wherein the orally acceptable solvent is ethanol.

11. The durable dental film-forming composition of claim 1, wherein the whitening agent comprises whitening particles ranging in size from about 0.1 μm to about 10 μm, wherein the whitening particles have a refractive index greater than about 12, and wherein the whitening particles are selected from the group consisting of titanium dioxide particles, zinc oxide particles, aluminum oxide particles, tin oxide particles, calcium oxide particles, magnesium oxide particles, barium oxide particles, silica particles, zirconium silicate particles, mica particles, talc particles, tetracalcium phosphate particles, amorphous calcium phosphate particles, alpha-tricalcium phosphate particles, beta-tricalcium phosphate particles, hydroxylapatite particles, calcium carbonate particles, zinc phosphate particles, silicon dioxide particles, zirconium silicate particles and combinations thereof.

12. The durable dental film-forming composition of claim 1, wherein the whitening agent is titanium dioxide and wherein the titanium dioxide is present in the composition in an amount ranging from about 0.05% to about 10% by weight.

13. The durable dental film-forming composition of claim 1, wherein the whitening agent is hydroxylapatite.

14. The durable dental film-forming composition of claim 1, wherein the whitening agent is a whitening complex comprising (a) hydrogen peroxide and (b) cross-linked polyvinylpyrrolidone.

15. The durable dental film-forming composition of claim 1, wherein the composition further comprises a therapeutic agent.

16. The durable dental film-forming composition of claim 15, wherein the therapeutic agent is selected from the group consisting of a fluoride ion source, a calcium source, a stannous ion source, a zinc ion source, a potassium ion source, an antibacterial agent and combinations thereof.

17. A durable dental film-forming composition, comprising:
an acrylate/octylacrylamide copolymer, wherein the acrylate/octylacrylamide copolymer is present in an amount of 9% or 10% by weight,
from about 4.5% to about 9% by weight, of an adhesive selected from a fully hydrogenated rosin and a partially hydrogenated rosin,
a whitening agent, which is titanium dioxide; and
an orally acceptable solvent, which is ethanol; and wherein the composition does not contain an alkyl cellulose ether.

18. A method of protecting a tooth surface from stains or bacteria in a human or animal comprising: applying the durable dental film-forming composition of claim 1 to a tooth surface in an oral cavity.

19. A method for whitening a tooth surface in a human or animal comprising: applying the durable dental film-forming composition of claim 1 to a tooth surface in an oral cavity.

* * * * *

UNITED STATES PATENT AND TRADEMARK OFFICE
CERTIFICATE OF CORRECTION

PATENT NO. : 10,596,098 B2
APPLICATION NO. : 15/344394
DATED : March 24, 2020
INVENTOR(S) : Rong Dong, Guofeng Xu and Shaotang Yuan It is certified that error appears in the above-identified patent and that said Letters Patent is hereby corrected as shown below:

In the Claims

In Column 13, Line 17, delete "12," and insert -- 1.2, -- therefor.

Signed and Sealed this
Thirteenth Day of February, 2024

Katherine Kelly Vidal
*Director of the United States Patent and Trademark Office*